(12) United States Patent
Allon

(10) Patent No.: US 8,033,827 B2
(45) Date of Patent: Oct. 11, 2011

(54) IMPLANT AND A METHOD FOR USING SAME

(76) Inventor: Dror M. Allon, Modi'in (IL)

( * ) Notice: Subject to any disclaimer, the term of this patent is extended or adjusted under 35 U.S.C. 154(b) by 193 days.

(21) Appl. No.: 12/357,095

(22) Filed: Jan. 21, 2009

(65) Prior Publication Data

US 2009/0186317 A1 Jul. 23, 2009

Related U.S. Application Data

(60) Provisional application No. 61/022,366, filed on Jan. 21, 2008.

(51) Int. Cl.
*A61C 8/00* (2006.01)
(52) U.S. Cl. ............... 433/173; 433/174; 623/17.17
(58) Field of Classification Search .......... 433/172–176, 433/201.1; 623/17.17
See application file for complete search history.

(56) References Cited

U.S. PATENT DOCUMENTS

| 4,523,910 | A | * | 6/1985 | Makovich | 433/80 |
| 4,671,768 | A | * | 6/1987 | Ton | 433/174 |
| 5,584,688 | A | * | 12/1996 | Sakuma et al. | 433/81 |
| 5,968,098 | A | * | 10/1999 | Winslow | 623/17.11 |
| 6,394,807 | B2 | * | 5/2002 | Robinson | 433/173 |
| 7,172,594 | B2 | * | 2/2007 | Biscup | 606/86 A |
| 2003/0104339 | A1 | * | 6/2003 | Fromovich et al. | 433/215 |
| 2004/0068324 | A1 | * | 4/2004 | Grundei | 623/32 |
| 2005/0192675 | A1 | * | 9/2005 | Robinson | 623/23.46 |
| 2006/0008773 | A1 | * | 1/2006 | Liao | 433/173 |

* cited by examiner

*Primary Examiner* — John J Wilson
(74) *Attorney, Agent, or Firm* — Browdy and Neimark, PLLC

(57) ABSTRACT

A novel dental implant for coupling an artificial tooth to a jawbone of a patient is provided and a method for using same. The implant comprises an elongated body having an apical end threaded bone-engaging portion for engaging the dental implant with said jawbone and preferably a coronal end that serves as a post or prothetic platform. The implant further comprises a skirt shaped semi-permeable membrane attached to the elongated body and is capable of being positioned in a first upwardly raised position and in a second downwardly spread position to provide a cover for a site surrounding the location at which said artificial tooth is to be implanted.

11 Claims, 5 Drawing Sheets

IMPLANT AND A METHOD FOR USING SAME

This application claims the benefit of provisional application Ser. No. 61/022,366, filed Jan. 21, 2008.

FIELD OF THE INVENTION

The present invention relates to dental implants and in particularly to methods and dental implants using bone grafting techniques.

BACKGROUND OF THE INVENTION

Dental implants have always been a subject for study and researches. In recent years the medical world has been investing a lot of effort to improve dental implants. The straightforward implant insertion procedure cannot be implemented when the edentulous alveolar ridge bone is insufficient, either in quality or quantity, (For example, fresh extraction sites, especially of multi-rooted or ankilosed teeth, that require more resection of bone to be accomplished). Furthermore, the high complication rates accompanying those cases, due to the anatomical proximity of the alveolar nerve or the maxillary sinus, poor bone quality and incorrect three-dimensional relation to the opposite dentition or ridge, are all important parameters in treatment plan considerations. Such cases are typically defined as sub-optimal alveolar ridge for implant insertion.

Under the conditions mentioned above (and others), augmentation of the future implantation site is necessary for long-term successes. This is done mostly by Guided Bone Regeneration (hereinafter "GBR"), using autogenic or allogenic bone grafting and/or allopllastic bone-substitute grafting and a biological barrier (membrane). The membrane is used for inhibition of connective-tissue proliferation into the grafted site thus, thereby creating better conditions for osteoinduction and osteoconduction by the grafting material.

The surgical procedure for GBR is technique-sensitive, and the failure rate and complication rate are considerably higher, comparing to the "simple" implant insertion procedure. Even when done by a specialist, the GBR procedure is still a time consuming procedure and thus very expensive for the patient. The surgical part of the treatment is usually divided into two or three sessions and lasts for several months. Some cases would require even more treatments due to arising complications.

By the conventional protocol of the GBR procedure of implanting a dental implant, after local anesthesia, the surgeon exposes the edentulous alveolar crestal bone at the future implant site. Granulation tissue is removed to prepare the bone defect to be grafted. Then autogenic bone harvested from other site. In the alternative, allograft bone/alloplast grafting material is prepared and applied to the defect. After designing the desired ridge contour, the graft is covered by membrane. When necessary, bone pins or screws are used to avoid migration of the bone particles or the membrane over the newly-shaped ridge. The flap has to be deliberately released by means of wide reflection, releasing cuts and periosteal scoring in order to cover the augmented alveolar crest without any tension. Failure to achieve this, results in the most common cause for the aforementioned complications (dehiscence, infection of the graft and failure to achieve the required quality and quantity of alveolar bone formation). Basically, the major difficulty lies with covering an enlarged volume of augmented bone with the same amount of soft tissue.

A second technical difficulty is the insertion of the dental implant at the same stage, since the ridge is not solid, but rather composed of a moist powder and small particles of bone or substitute. It neither can hold nor can be arranged properly around the implant and still be covered by the membrane and the mucoperiosteal flap. Mainly due to this reason, only after four to nine months, (once the bone graft is consolidated and replacement resorption by natural host bone cells occurs to some extent) a second intervention is performed. In this stage, after local anesthesia and second exposure of the bone by flap reflection, serial drills into the newly reconstructed ridge are followed by the insertion of the dental implant. Next, the flap is sutured over the implant and an additional healing period of three to six months is usually required.

After the latter healing period, a third surgical intervention is needed for the implant head exposure and the connection of a trans-mucosal part as a healing cup, which is than replaced after few weeks by a prosthetic platform for restoration of the tooth. This stage requires local anesthesia and sutures, as well. Hence a total of three surgeries and three appointments for suture removal are usually needed while carrying out the conventional procedure.

Nowadays, most dental implants are made of Titanium and are shaped as a cylinder or a screw. Bone grafting materials are commercially available in various forms and consistencies as allografts or alloplasts delivered as block, powder, grains, putty or gel. Some of the materials require preparation or manipulation during surgery, rendering them exposed to the non-sterile environment of the dental clinic and to an increased contamination risk. Delivery of the grafted material is usually done by dental spatula or special syringe which is neither accurate nor efficient.

Polypeptide growth factors are recombinant biologic mediators that regulate cellular activity. They include growth factors (e.g. PDGF, TGF-$\beta$, igf-1, vegf and the like), differentiation factors (e.g. BMP-2, OP-1, GDF-5, GDF-7), matrix factors (such as fibronectin, vitronectin, thrombobospondin-1) and platelets-rich plasma ("PRP"). Recent studies demonstrated induction of bone growth by rhBMP-2, carried by injectable collagen or semisolid calcium-phosphate cement, in craniofacial and dentoalveolar defect in animals model and human.

Recently, commercially available rhBMP-2 (Induct-os®, INFUSE®) and op-1® putty were approved for clinical use by the FDA, Some of them for maxillofacial application.

Another crucial part of the above-described procedure is the GBR membranes, which are available as sheath or mesh of absorbable (collagen) or non-absorbable material (such as PTFE or Titanium). The membrane has to be molded in the three-dimensional form of the augmented ridge and the adjacent implants or teeth. This time consuming process is carried out by trial and error during the operation. Another fact that makes working with the GBR membrane even more difficult is that most of the absorbable membranes, when become wet, turn out to be softer and more difficult for manipulation. In certain cases the membrane has to be fixated to the surrounding bone by mean of miniature pins or screws to avoid graft mobility and leakage. Again, the exposure time of the grafted area and the membrane during these trials affect the total operation time, and increase the chances of post operative infection as well as other complications.

Several methods and implants using bone grafting techniques are known in the art, for example U.S. Pat. No. 6,722,884 discloses a method for preserving the alveolar ridge surrounding a presently extracted root socket by backfilling the socket with bone grafting material and installing an implant in the root socket area. As described in this publication, the dental implant may be installed apically into the root socket immediately following root extraction. The open area of the root socket surrounding the implant is then backfilled with bone grafting material immediately after the implant placement. In the alternative, the presently extracted root socket is filled with bone grafting material, the bone-growth is promoted in the root socket by the bone grafting material for 2-12 months. Then, after sufficient bone growth has been promoted, an implant is installed in the extraction site area in the normal manner.

Another publication that relates to bone grafting technique is US 20060008773 which describes a titanium-mesh umbrella for bone grafting used to combine with conventional implant and to hold bone grafting material in proper position during dental implant placement procedure. The titanium-mesh umbrella forms a projecting umbrella surface with a curvature in perpendicular direction. After the titanium metal umbrella has been positioned a guide tissue membrane can than be securely attached and a space for bone growth can be maintained.

However, there is still a need for an implant and a procedure for using it that is less time consuming and consequently would reduce the costs associated therewith would lower the complications rate.

SUMMARY OF THE INVENTION

It is object of the present invention to provide a dental implant and methods for its use, for performing a safer and less time consuming dental implantation procedure in areas require bone grafting.

It is another object of the present invention to provide methods and a dental implant to enable injecting grafting material in a clean and sterile way from a sealed container to the designated graft bed without exposing the grafting material to oral contamination.

It is yet another object of the present invention to provide a dental implant and methods, for simplifying the placement of biological barrier, a step which is a rather complicated step in existing GBR procedures, which in turn minimize the exposure of the membrane to contaminations.

It is still another object of the invention to provide a novel implant for reconstruction the dentition in areas of sub-optimal edentulous ridge which will enable improving conventional procedures.

It is another object of the present invention to provide a dental implant that comprises all components required in the process in one sterilized package.

Other objects of the invention will become apparent as the description of the invention proceeds.

According to the first embodiment of the present invention there is provided a dental implant for coupling an artificial tooth to a jawbone of a patient which comprises:

(i) an elongated body having a first (apical) end threaded bone-engaging portion for engaging the dental implant with said jawbone and a second (coronal) end that serves as a post or prothetic platform, preferably made of Titanium and designed to provide initial mechanical stability; and (ii) a skirt shaped semi-permeable membrane, preferably made of collagen, and attached to the elongated body at the junction between the post and the threaded ends, and adapted to be positioned either in a first upwardly raised position or in a second downwardly spread position, where the latter position is adapted to provide a cover for a site surrounding the location at which the artificial tooth is to be implanted and preferably the alveolar ridge to be augmented.

According to another preferred embodiment of the present invention, the second (coronal) end elongated body provided with a second end adapted to be detachably connected to a reservoir containing bone grafting material, and wherein the elongated body comprises circumferentially located openings to allow discharge of the bone grafting material, and wherein the skirt shaped semi-permeable membrane, when positioned in that second downwardly spread position, is capable of forming together with the upper surface of the native host bone to which the first end of elongated body would be affixed, an enclosure at which the bone grafting material is to be discharged via these openings.

By another preferred embodiment, the second end of the elongated body comprises a holding means adapted to hold a temporary crown or a healing cup after detaching the reservoir of the bone grafting material.

According to still another embodiment, the dental implant further comprising a one-way valve adapted to prevent backward reflux of the discharged grafting material from the site at which the grafting material would be discharged back towards the reservoir.

By yet another embodiment the dental implant further comprising a spacer (e.g. a ring) for connecting the skirt shaped semi-permeable membrane to the elongated body of the dental implant and for maintaining a space between the elongated body and the skirt shaped semi-permeable membrane.

In accordance with another preferred embodiment of the present invention the skirt shaped semi-permeable membrane comprises a connective tissue. Preferably, the skirt shaped semi-permeable membrane is made of collagen.

According to still another embodiment, the dental implant base/container further comprises a duct and pump system for sterilely delivering the bone grafting material from the reservoir towards the enclosure, at which the bone grafting material is to be discharged.

By yet another embodiment of the present invention one or more of the circumferentially located openings at the elongated body of the dental implant are backwardly tilted and/or located essentially above the threads of the dental implant in order to avoid bone particles from blocking these openings during insertion of the implant.

According to another aspect of the present invention there is provided a method for carrying out a dental implantation procedure which comprises the steps of:

a. drilling a cavity at a site in a patient's jawbone for inserting thereat a first (apical) end of a dental implant. The drilling of the cavity is carried out at the designated site, and the cavity should have proper dimensions to allow safe, yet stable positioning of the dental implant thereat. The drilling is preferably carried out by using an appropriate implant speed-reduced physio-dispenser driven torque-controlled handpiece into the residual ridge to the desired (or available) depth and angle according to the planned prosthodontic restoration.

b. Positioning the dental implant while the attached skirt shaped semi-permeable membrane is in an upwardly raised position, by affixing the first (apical) end of the dental implant to a native host bone at that site. This may be done by using a torque-controlled handpiece at a low speed.

c. Upon inserting the dental implant at its position and positioning the skirt shaped semi-permeable membrane in the downwardly position, one should take care that it covers all bone-defect edges.

d. suturing the flap formed (preferably in a water-tight and tension-free fashion) over the still loose skirt shaped semi-permeable membrane being in its downwardly spread position;
e. filling a space defined by the implant, the membrane and the surrounding with a bone grafting material delivered through the implant; and
f. placing a temporary crown on top of the dental implant. In case that the dental implant is not yet ready for full occlusal load, a healing cup would be placed instead.

Preferably, the step of filling a space comprises inserting a pump shaft adapter for driving a pump to deliver the grafting material from the container through the implant into a space defined by the implant, the membrane and the surrounding bone. While the material is pressurized in the defined, closed grafting space, resistance to the pump operation is progressively built until it reaches a pre-defined level set by means of maximum revolving torque of the headpiece. One of the major advantages associated with this embodiment is that it prevents from overfilling the grafting space.

In accordance with another preferred embodiment of the invention, the method provided is adapted for carrying out a dental implantation procedure at a site that requires bone grafting and wherein by positioning the skirt shaped semi-permeable membrane in the downwardly spread position it would form together with the native host bone to which the dental implant has been affixed, an enclosure at which a bone grafting material is to be discharged. By this embodiment, the method further comprises a step of discharging, prior to carrying out the step of placing the temporary crown, the bone grafting material via at least one opening located at the circumference of the dental implant into the enclosure described above, Preferably, the bone grafting material is discharged from a reservoir containing the bone grafting material that is detachably connected to the dental implant.

By yet another preferred embodiment, the bone grafting material is discharged (e.g. injected) into the enclosure formed between the partially exposed native host bone and the skirt shaped semi-permeable membrane, after being conveyed from the reservoir containing the bone grafting material through a duct system and discharged through at least one opening located at the circumference of the dental implant underneath the skirt shaped semi-permeable membrane. This way, the introduction of the bone grafting material is carried out in a sterile way while preventing the exposure of the grafting material to oral contaminations.

According to another embodiment of the present invention drilling, affixing of the dental implant (e.g. by screwing it to the native host bone) and motorizing of the pump main shaft is carried out by using a low speed dental handpiece provided with torque control. The reason, being to avoid over-drilling, over screwing and over filling in proximity to the alveolar nerve and to the maxillary sinus.

In accordance to another embodiment of the present invention, the grafting material which is use for bone regeneration (GBR) using autogenic or allogenic bone graft and/or allopllastic bone-substitute grafting material) and a biological barrier (membrane), may either be prepared and sterilely packed as a part of the product, or be prepared before the implantation procedure starts, and stored in the reservoir which is comprised in the dental implant.

According to another embodiment of the present invention, the bone grafting material is injected by using a novel "pressure casting" technique.

BRIEF DESCRIPTION OF THE DRAWINGS

For a more complete understanding of the present invention, reference is made to the following detailed description taken in conjunction with the accompanying drawing wherein.

DETAILED DESCRIPTION OF PREFERRED EMBODIMENTS

For a more complete understanding of the present invention, reference is made to the following detailed description taken in conjunction with the accompanying drawings.

Let us first consider a case where an artificial tooth should be implanted where the jawbone has a defect and therefore the procedure must include bone grafting stage as well.

Figure 1:
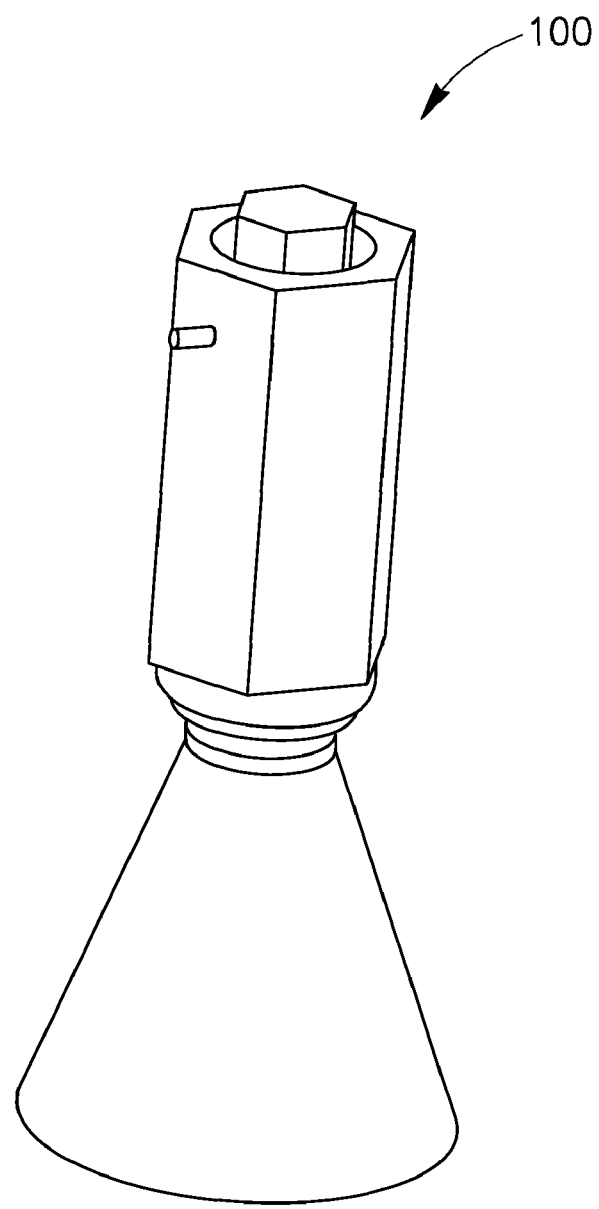
FIG. 1—presents schematic view of a dental implant according to the present invention.
Figure 2:
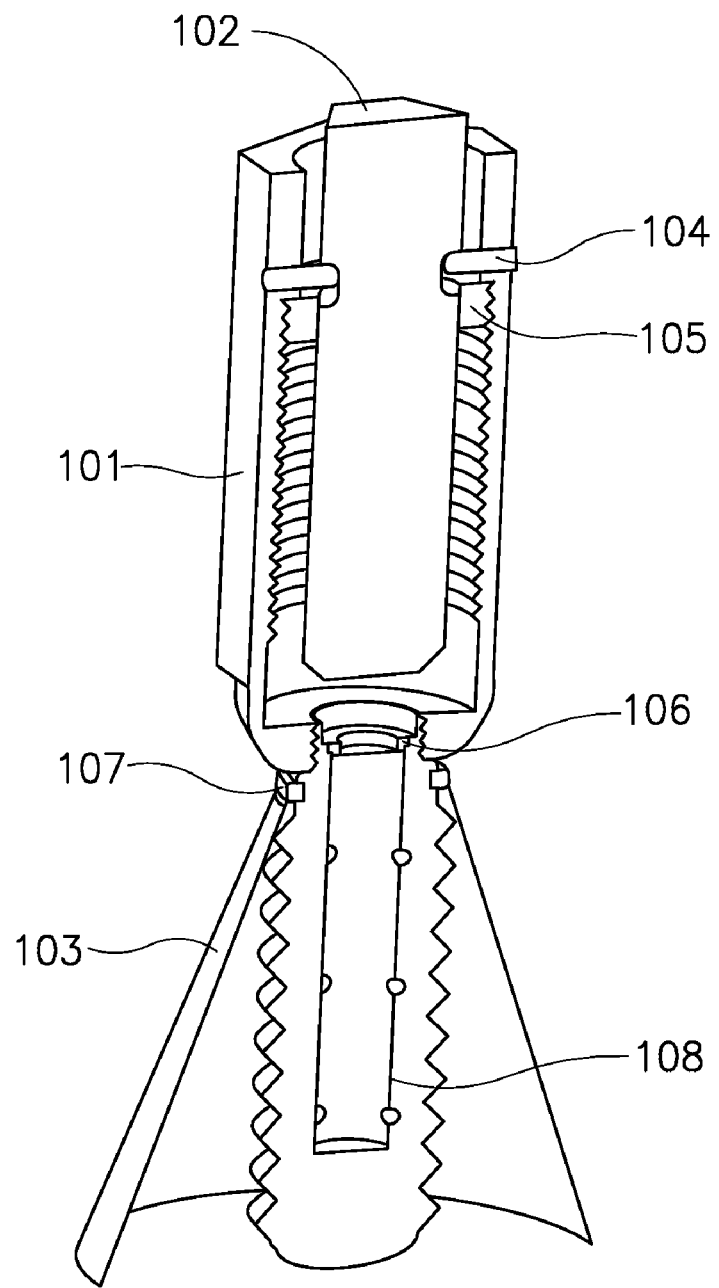
FIG. 2—presents a cross section view of the dental implant shown in FIG. 1.
Figure 3:
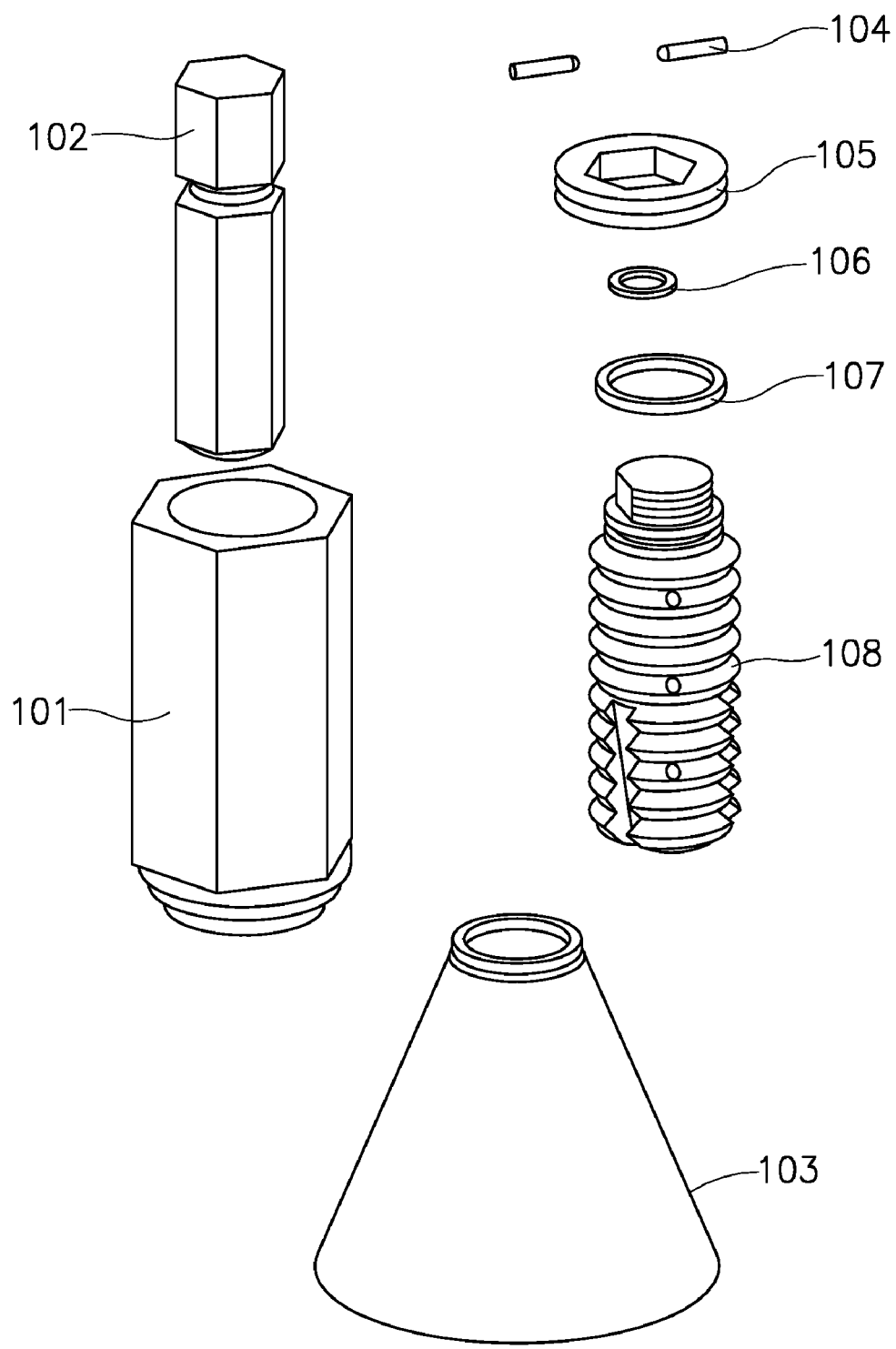
FIG. 3—presents an exploded view of the dental implant shown in FIG. 1.

FIGS. 1-3 present non-limiting examples of schematic views of dental implants construed in accordance with certain embodiments of the present invention for the case referred to above. Dental implant (100) of the present invention comprises a base/reservoir (101) which is preferably designed to fit dental handpiece and can be detached from the rest of the dental implant once the implant is firmly positioned and the bone grafting material has been injected. The base/reservoir (101), comprises a pumping means to enable the discharge of the bone grafting materials from the reservoir. Once the implant has been affixed to its position, the handpiece is connected to the head of the main shaft 102 that extends outwardly from base/reservoir 101. Screwing the main shaft with the handpiece, (e.g. a device that is torque controlled, as known in the art per se) causes disk 105, which acts as a piston, to be driven along main shaft 102 to the internal lumen of the implant, thereby pushing the bone grafting material to be outwardly discharged from the reservoir. A skirt shaped semi-permeable membrane (103), preferably made of a connective tissue such as collagen, is attached to the elongated body (the screw-type implant). The skirt membrane 103 may be positioned in at least two distinctive positions, where the plane at the narrow end of the membrane may be viewed as an axis around which the membrane may change its position from a first upwardly raised position to a second downwardly spread position (and vice versa). The raised mode is preferably used as the initial mode wherein the membrane is contracted to minimize the distance between the wide end of the skirt and the dental implant, in order not to block the surgeon's point of view, thereby enabling the surgeon to affix the dental implant to the jawbone at the optimal location and angle. The spread (downward) position is preferably used after the dental implant has been affixed to the jawbone, and is used to provide a cover for a site surrounding the location at which said artificial tooth is to be implanted. Membrane 103 may further serve as a biological barrier to inhibit connective tissue growth and to guide bone regeneration in the space defined between the implant and the alveolar bone defect in the subperiosteal plane. In addition, the membrane may be made of a semi permeable material and may either be absorbable or non absorbable. As will be appreciated by those skilled in the art, although the shape of the membrane has been described herein as a skirt, any other applicable shape such as a bell or others may be used as long as it is able to function in the manner described above.

In the upper part of the base/reservoir 101 there is one or more affixing pins (104) to stabilize the main shaft (102) while being screwed by the handpiece. As was mentioned before, disk (105) is connected to the reservoir and by moving along the main shaft it presses the grafting material to the internal lumen of the implant and through number of tunnels spreading the grafting material towards the defect to be augmented. Below the reservoir there is a one-way-valve (106), designed to prevent backward reflux of the biomaterial from the internal lumen to the reservoir. In addition a spacing ring (107) connects the skirt membrane to the implant and maintains space between the implant and the membrane.

The lower part of the dental implant comprises a screw-type Titanium portion (108) that is adapted to be screwed into the edentulous alveolar ridge bone. The screw-type Titanium portion has an internal lumen and number of tunnels that direct the grafting material from the reservoir through the internal lumen to the augmented bone defect.

Once the space of the augmented bone defect has been filled with the bone grafting material, any further introduction of bone grafting material builds us a pressure in that confined space. Once this pressure (when translated into resistance force) reaches the pre-defined level of the torque control handpiece, the main shaft will not be screwed any further and the handpiece may then be removed.

Figure 4:
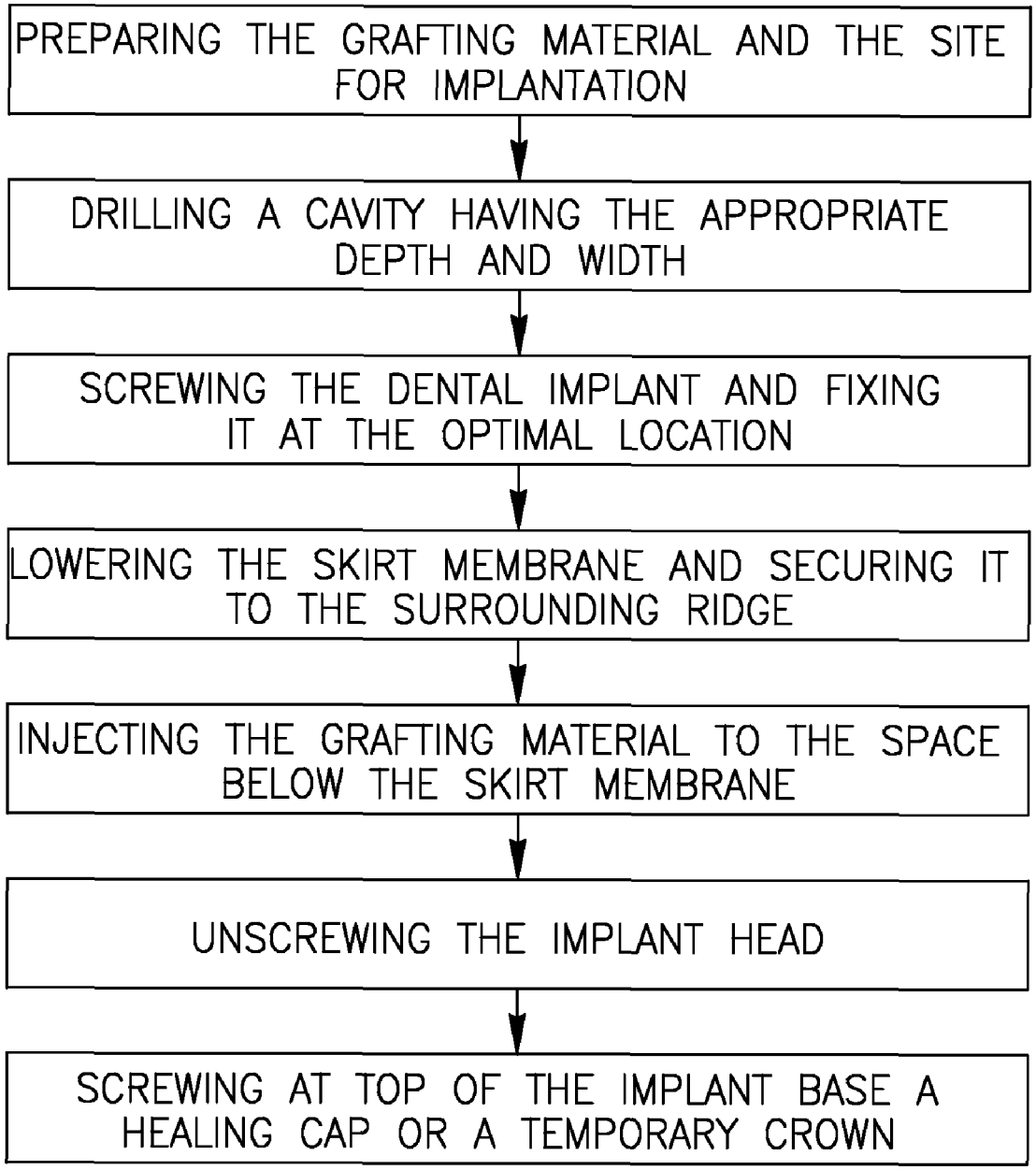
FIG. 4—presents a flow chart of the method provided by the present invention.
Figure 5A:
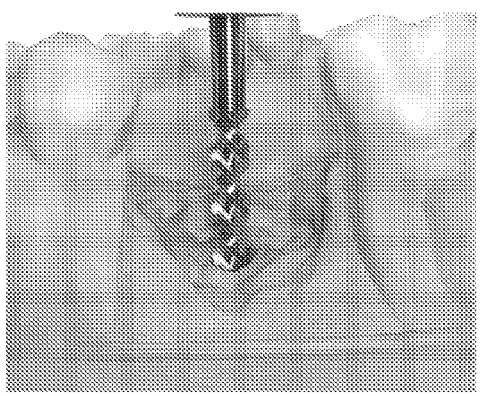
FIGS. 5A to 5E—presents steps in the method provided by the present invention.
Figure 5B:
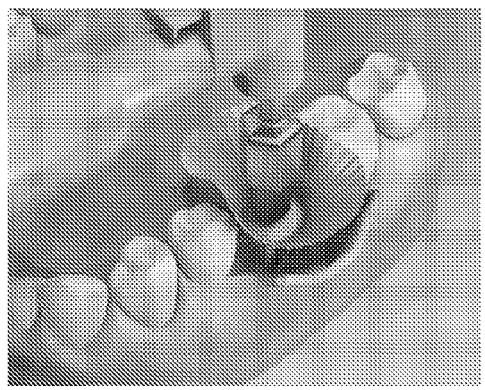
Figure 5C:
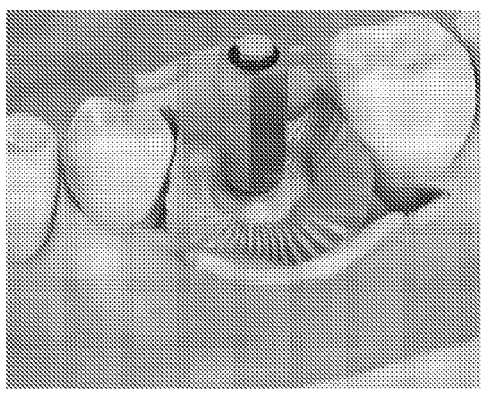
Figure 5D:
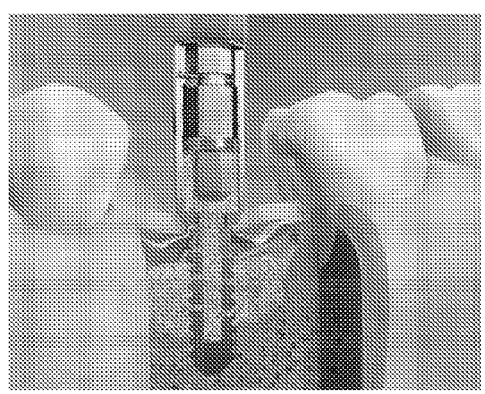
Figure 5E:
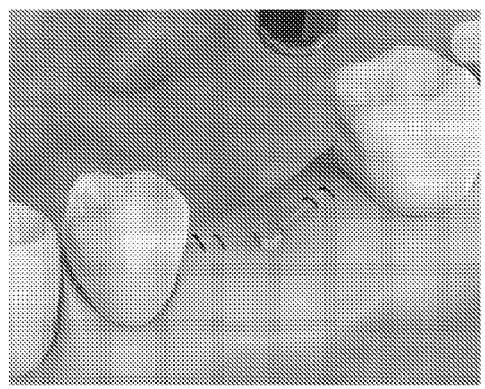

FIG. 4. presents a flow chart describing the steps in the implantation procedure in accordance with the present invention, to enable carrying out all the aforementioned stages within only one simpler and shorter session. Similarly, FIGS. 5A to 5E present various stages while carrying out the method provided by the present invention. The first step in FIG. 4 is the preparation step (410) wherein the grafting material is being prepared and filled in the reservoir and the lumen is filled with osteoinductive factors and/or osteoconductive allograft/alloplast grafting materials. The reservoir is then closed and the skirt membrane is confirmed to be in its raised and contracted mode. However, the preferred way of implementing the method provided by the present invention is by using (at the dental clinic) a sealed container provided with the bone grafting material in a ready to use form, rather than to prepare the grafting material under the dental clinic conditions. Another possible alternative could be using a sealed container that comprises the grafting material, and adding saline through a nozzle protruding to that container, to the grafting material.

In step (420), the future site is exposed for grafting and for implant insertion and the granulation tissue is removed. The drilling of a cavity is then carried out with appropriate implant speed-reduced physio-dispenser driven handpiece into the residual ridge to the desired depth, width and angle according to the prosthodontic restoration plan. Following the drilling the implant is screwed (step 430) and located to its optimal location and angle from a prosthodontic point of view, regardless of alveolar ridge form and condition. This step is preferably carried out by using a power-driven handpiece, with speed reduction and torque-control, according to any method known in the art per se. The insertion of the implant is carried out in this step under direct line of sight as the skirt shaped semi-permeable membrane in its raised position.

Once the implant is affixed to the prepared site, the skirt membrane is lowered from its upwardly raised position into its spread mode (440). During this step, the membrane is flipped around the implant and the surrounding ridge like a tent over a central column followed by suturing the flap over the membrane and circumferentially to the supragingival post. The flap is sutured in a water-tight and tension-free fashion over the still-loose membrane, leaving the implant head ("post") exposed. Upon securing the skirt membrane, the handpiece insertion adapter is replaced with a pump shaft adapter and is employed to drive the pump and deliver the semi-solid grafting material (step 450) from the container through the implant and into the space defined by the implant, the membrane and the surrounding bone. This grafting material is injected through openings (e.g. tunnels) to the surrounding grafting space (the outlet tunnels are angled backward and located at the upper part of the implant threads to avoid bone particles from blocking them during the introduction of the implant). However, after inserting the implant, if there are openings located too close to the implant bottom end, they will anyway be blocked by the jawbone bone to which the implant has been screwed (depending of course of the bone local height at that particular point) and since no bone grafting is required at that point (as the bone is already at that height) they opening will be blocked preventing the bone grafting material from flowing outwardly, and only where the openings are not blocked by the bone, i.e. areas which require augmentation, will be filled by using this mechanism. The one-way-valve prevents the grafting material to reflux backwards, to the reservoir. Among the advantages associated with this type of a procedure one may consider the following:

Neither membrane design nor fixation to the implant or to the bone is of importance, as the material is discharged underneath the sutured flap.

Manipulation and delivery of the bone grafting material is done automatically, at accurate amount and in a timely efficient manner.

At the end of this stage, the grafting material is well condensed around the implant, sealed by the membrane and in direct contact with the grafted bony bed, which is the source for osteoblast cells for guided regeneration.

The following drawbacks that are associated with prior art methods such as overfilling of bone grafting material, over tension of the flap, exposure of the sterilized bone grafting material, the need for wide flap exposure and release and technically demanding manipulation of the semi solid components, may all be avoided by using the present invention.

Next, the head of the implant (the base/reservoir and the main shaft) is unscrewed and detached from the implant (460), followed by screwing (470) a healing cup over the post or preparation and cementation of a conventional temporary crown, depending on whether the implant is stable enough to hold the conventional temporary crown.

Therefore, the one-piece implant/post design described in this example offers the following advantages:

i) No microscopic gap is left between the two structures in the biological width adjacent to the crestal peri-implant bone, where such gaps were found to encourage crestal bone resorption around the implant in the long term; and ii) Special anti-rotation mechanisms of internal or external hexagons and screws are currently used by the prior art methods to interconnect the two structures. Unfortunately, structural failure of these mechanisms due to overload is rather common. This in turn might jeopardize the whole long lasting and expensive surgical effort due to premature breakdown of the implant hexagon or shearing the connecting mini-screw inside the implant, despite the fact that the implant is well anchored by means of osseointegration into the alveolar bone. Such mechanisms become redundant for the device of the present invention and the way it is applied.

It is to be understood that the above description only includes some embodiments of the invention and serves for its illustration. Although the present invention has been described with reference to presently preferred embodiments and practices, it should be understood that various changes and modifications may be devised by a person skilled in the art without departing from the scope of the present invention, and are thus encompassed by the present invention. In particularly, although the implant has been described herein and throughout the specification and claims as being a dental implant, it should be understood to encompass also implants for use in other medical fields such as orthopedic, plastic surgery, neurosurgery and the like, mutatis mutandis.

The invention claimed is:

1. A dental implant for coupling an artificial tooth to a jawbone of a patient which comprises:
   (i) an elongated body having a first end threaded bone-engaging portion for engaging the dental implant with said jawbone; and
   (ii) a skirt shaped semi-permeable membrane attached to said elongated body and is capable of being positioned in a first upwardly raised position or in a second downwardly spread position to provide a cover for a site surrounding the location at which said artificial tooth is to be implanted,
   wherein a second end of said elongated body is adapted to be detachably connected to a reservoir containing bone grafting material, wherein said elongated body comprises circumferentially located openings to allow discharge of the bone grafting material and wherein the skirt shaped semi-permeable membrane, when positioned in that second downwardly spread position, is capable of forming together with the upper surface of the native host bone to which the first end of elongated body would be affixed, an enclosure at which the bone grafting material is to be discharged via these openings.

2. A dental implant according to claim 1, wherein said second end comprises a holding means adapted to hold a temporary crown or a healing cup after detaching said reservoir.

3. A dental implant according to claim 1, further comprising a one way valve adapted to prevent backward reflux of said discharged grafting material from said site back towards said reservoir.

4. A dental implant according to claim 1, further comprising a spacer for connecting said skirt shaped semi-permeable membrane to said elongated body of the dental implant and for maintaining a space between said elongated body and said skirt shaped semi-permeable membrane.

5. A dental implant according to claim 1, wherein said skirt shaped semi-permeable membrane comprises collagen.

6. A dental implant according to claim 1, wherein one or more of said openings are backwardly tilted and located essentially above the threads of the dental implant.

7. A dental implant according to claim 1, wherein said elongated body further comprises a cavity to enable conveying bone grafting material therethrough towards the site surrounding the location at which said artificial tooth is to be implanted.

8. A method for carrying out a dental implantation procedure which comprises the steps of:
   a. drilling a hole at a site in a patient's jawbone for inserting thereat a first end of a dental implant;
   b. positioning a skirt shaped semi-permeable membrane attached to said dental implant in an upwardly raised position and locating said dental implant at its position by affixing said first end of the dental implant to a native host bone at said site;
   c. upon affixing said dental implant at its position, positioning said skirt shaped semi-permeable membrane in a downwardly spread position;
   d. suturing a flap over the skirt shaped semi-permeable membrane being in its downwardly spread position;
   e. filling a space defined by the implant, the membrane and the surrounding with a bone grafting material delivered through the implant; and
   f. placing a temporary crown on top of said dental implant.

9. A method according to claim 8, wherein the bone grafting material is delivered via one or more openings located at the circumference of the dental implant, into an enclosure formed by said skirt shaped semi-permeable membrane positioned in said downwardly spread position and upper surface of the native host bone to which the dental implant has been affixed.

10. A method according to claim 8, wherein said grafting material is discharged from a reservoir containing the bone grafting material that is detachably connected to said dental implant.

11. A method according to claim 8, wherein the discharge of the bone grafting material into a space defined by the implant, the membrane and the surrounding bone is torque controlled.

* * * * *